(12) United States Patent
Ariga et al.

(10) Patent No.: US 9,554,711 B2
(45) Date of Patent: Jan. 31, 2017

(54) SPHYGMOMANOMETER AND CHARGING UNIT FOR SPHYGMOMANOMETER

(75) Inventors: Hiroyasu Ariga, Kyoto (JP); Yoshihiko Sano, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 548 days.

(21) Appl. No.: 13/100,613

(22) Filed: May 4, 2011

(65) Prior Publication Data

US 2011/0208068 A1    Aug. 25, 2011

Related U.S. Application Data

(63) Continuation of application No. PCT/JP2009/066011, filed on Sep. 14, 2009.

(30) Foreign Application Priority Data

Nov. 4, 2008  (JP) ................... 2008-283351

(51) Int. Cl.
*A61B 5/02*     (2006.01)
*A61B 5/022*    (2006.01)
(Continued)

(52) U.S. Cl.
CPC .......... *A61B 5/02233* (2013.01); *A61B 5/021* (2013.01); *A61B 5/0225* (2013.01); *A61B 2560/0214* (2013.01); *A61M 2230/30* (2013.01)

(58) Field of Classification Search
CPC .......................... A61B 5/021; A61M 2230/30
(Continued)

(56) References Cited

U.S. PATENT DOCUMENTS 5,934,908 A * 8/1999 Woog et al. ................. 433/216
6,114,832 A * 9/2000 Lappi et al. ................. 320/108
(Continued)

FOREIGN PATENT DOCUMENTS

JP     07-163531 A     6/1995
JP     08-323657 A    12/1996
(Continued)

OTHER PUBLICATIONS

Patent Abstracts of Japan, Publication No. 07-163531, Publication Date: Jun. 27, 1995, 1 page.
(Continued)

*Primary Examiner* — Jacqueline Cheng
*Assistant Examiner* — Puya Agahi
(74) *Attorney, Agent, or Firm* — Osha Liang LLP

(57) ABSTRACT

A sphygmomanometer includes an expandable/contractable air bag supplied with air; a bag-shaped cover body for accommodating the air bag and for attaching the air bag to a site to be measured; an expansion and contraction mechanism for expanding and contracting the air bag; and a power supply unit arranged in the bag-shaped cover body. The power supply unit includes a battery for supplying driving power to the expansion and contraction mechanism, and a non-contact power reception unit for receiving power for charging the battery. The non-contact power reception unit is supplied with power through an electromagnetic inductive action from a non-contact power transmission unit arranged in a non-contact state with the non-contact power reception unit.

7 Claims, 11 Drawing Sheets

(51) Int. Cl.
*A61B 5/021* (2006.01)
*A61B 5/0225* (2006.01)
(58) Field of Classification Search
USPC .......................................... 600/301, 489–499
See application file for complete search history.

(56) References Cited

U.S. PATENT DOCUMENTS

| | | | |
|---|---|---|---|
| 6,379,310 B1* | 4/2002 | Mori et al. ................. | 600/490 |
| 7,109,682 B2 | 9/2006 | Takagi et al. | |
| 7,615,010 B1* | 11/2009 | Najafi et al. ................ | 600/481 |
| 2005/0189910 A1* | 9/2005 | Hui ............................. | 320/108 |
| 2005/0283084 A1* | 12/2005 | Kato ........................... | 600/499 |
| 2006/0058687 A1 | 3/2006 | Kishimoto et al. | |
| 2006/0079792 A1* | 4/2006 | Finburgh et al. ........... | 600/485 |
| 2006/0111636 A1* | 5/2006 | Jacober et al. ............. | 600/490 |
| 2006/0142808 A1* | 6/2006 | Pearce et al. ............... | 607/5 |
| 2006/0217617 A1 | 9/2006 | Wachtenberg | |
| 2006/0272664 A1* | 12/2006 | O'Dwyer ............ | A45D 29/007 132/73.6 |
| 2007/0247312 A1* | 10/2007 | Sekine ........................ | 340/572.1 |
| 2008/0208065 A1* | 8/2008 | Aebersold et al. ......... | 600/488 |
| 2008/0209650 A1* | 9/2008 | Brewer et al. .............. | 15/22.1 |
| 2008/0298603 A1* | 12/2008 | Smith .......................... | 381/67 |
| 2009/0102419 A1* | 4/2009 | Gwon et al. ................ | 320/108 |
| 2009/0118779 A1* | 5/2009 | Najafi et al. ................ | 607/2 |

FOREIGN PATENT DOCUMENTS

| | | |
|---|---|---|
| JP | 2006-081655 A | 3/2006 |
| JP | 2006-314181 A | 11/2006 |
| JP | 2007-275227 A | 10/2007 |
| WO | 2004/100783 A1 | 11/2004 |

OTHER PUBLICATIONS

Patent Abstracts of Japan, Publication No. 2006-314181, Publication Date: Nov. 16, 2006, 1 page.
Patent Abstracts of Japan, Publication No. 08-323657, Publication Date: Dec. 10, 1996, 1 page.
Patent Abstracts of Japan, Publication No. 2007-275227, Publication Date: Oct. 25, 2007, 1 page.
Patent Abstracts of Japan, Publication No. 2006-081655, Publication Date: Mar. 30, 2006, 1 page.
English abstract of WO2004/100783A published on Nov. 25, 2004, 1 page.
International Search Report issued in PCT/JP2009/066011 mailed on Oct. 13, 2009, and English translation thereof, 2 pages.
Office Action issued in corresponding Russian Application No. 2011-122632/14(033521) dated Jul. 22, 2013, and English translation thereof (7 pages).

* cited by examiner

SPHYGMOMANOMETER AND CHARGING UNIT FOR SPHYGMOMANOMETER

TECHNICAL FIELD

The present invention generally relates to sphygmomanometers and charging units for sphygmomanometers, and more specifically to a sphygmomanometer including a chargeable battery inside a cuff, and a charging unit for the sphygmomanometer.

BACKGROUND ART

The conventional sphygmomanometer includes a cuff-integrated sphygmomanometer (patent document 1) disclosed in Japanese Unexamined Patent Publication No. 7-163531 aimed to prevent the cuff from moving around and shifting when attaching the cuff and enable the cuff to be easily attached. In the sphygmomanometer disclosed in patent document 1, a case body including a main body lower case and a main body upper case is fixed to the cuff. A battery, a pressurization pump, an electromagnetic valve, a circuit substrate, a display, or the like are arranged inside the main body upper case.

Japanese Unexamined Patent Publication No. 2006-314181 discloses a non-contact type charging device aimed to simultaneously charge using one non-contact type power transmission device of a plurality of portable electronic devices attached to a non-contact type power reception module (patent document 2). The non-contact type charging device disclosed in patent document 2 includes a non-contact type power transmission device with a primary coil connected to a regulator circuit, and a non-contact type power reception module in which rectifying means connected to a secondary coil that magnetically couples with the primary coil is modularized, where the secondary batteries in a plurality of portable electronic devices are charged through the rectifying means.

Japanese Unexamined Patent Publication No. 8-323657 discloses a micro-robot aimed to provide a system for performing charging and communication of a built-in battery (patent document 3). The micro-robot disclosed in patent document 3 includes two micro-drive units, each micro-drive unit including a distributed stepping motor. The charging of the secondary power supply built in the robot and the communication between the coils are performed using an excitation coil of the motor.

Patent Document 1: Japanese Unexamined Patent Publication No. 7-163531
Patent Document 2: Japanese Unexamined Patent Publication No. 2006-314181
Patent Document 3: Japanese Unexamined Patent Publication No. 8-323657

SUMMARY OF INVENTION

In the sphygmomanometer disclosed in patent document 1, the battery, the pressurization pump, the electromagnetic valve, or the like are integrally arranged on an arm band (cuff). With such a configuration, the sphygmomanometer can be easily handled, and a user can easily measure the blood pressure. Furthermore, the battery is accommodated in the case body fixed to the cuff in the sphygmomanometer disclosed in patent document 1, but the battery is preferably accommodated inside the cuff so that the sphygmomanometer can be miniaturized.

If the secondary battery that can be charged as a drive battery is used in such a sphygmomanometer where the main body of the sphygmomanometer and the cuff are integrated, a dedicated charging device needs to be prepared and the charging device needs to be connected to the cuff every time the charging is carried out. In this case, however, much time and efforts are required when charging the battery, which may increase the load on the user of the sphygmomanometer.

Furthermore, if the secondary battery is used as the battery, a terminal for connection with respect to the charging device needs to be provided in the cuff. In this case, the terminal may degrade through repeated connection, and connection failure may occur if water or dust attaches to the terminal.

Therefore, one or more embodiments of the present invention provides a sphygmomanometer in which the secondary battery can be charged through a simple operation and with high reliability, and a charging unit for the sphygmomanometer.

A sphygmomanometer according to one or more embodiments of the present invention includes an expandable/contractable fluid bag supplied with fluid; a bag-shaped cover body for accommodating the fluid bag and for attaching the fluid bag to a site to be measured; an expansion and contraction mechanism for expanding and contracting the fluid bag; and a power supply unit arranged inside the bag-shaped cover body. The power supply unit includes a secondary battery for supplying driving power to the expansion and contraction mechanism and a power reception unit for receiving power for charging the secondary battery. The power reception unit is supplied with power through an electromagnetic inductive action from a power transmission unit arranged in a non-contact state with the power reception unit.

According to the sphygmomanometer configured as above, a terminal for connection with respect to the charging device does not need to be arranged at the sphygmomanometer by using a non-contact type charging method. Thus, a case body (housing) for arranging the terminal is unnecessary, and a configuration in which the power supply unit is arranged inside the bag-shaped cover body can be easily adopted. The connection failure, the lowering of the charging efficiency, or the like that arise from the terminal for connection do not need to be taken into consideration, and thus, the secondary battery can be charged at high reliability. Furthermore, the task at the time of charging the secondary battery can be easily carried out because the connection of the sphygmomanometer and the charging device is not necessary.

According to one or more embodiments of the present invention, the expansion and contraction mechanism is arranged inside the bag-shaped cover body. According to the sphygmomanometer configured as above, the miniaturization of the sphygmomanometer can be advantageously put forth.

According to one or more embodiments of the present invention, the power reception unit includes a flexible substrate having flexibility and being formed with a coil on the surface. According to the sphygmomanometer configured as above, the power reception unit can easily lie along the shape of the bag-shaped cover body with the fluid bag attached to a site to be measured.

According to one or more embodiments of the present invention, the power reception unit has a power transmission and reception function enabling transmission and reception of power when the power reception units are positioned proximate to each other between the plurality of sphygmomanometers. According to the sphygmomanometer configured as above, the lack of power can be compensated among the plurality of sphygmomanometers even in a place where the charging device is not arranged.

A charging unit for a sphygmomanometer according to one or more embodiments of the present invention includes the sphygmomanometer according to any one of the above, and a charging device for charging the secondary battery. The charging device includes a positioning unit positioned with respect to the bag-shaped cover body, and a power transmission unit, arranged to face the power reception unit in a non-contact state when the positioning unit is positioned with respect to the bag-shaped cover body, capable of supplying power to the power reception unit through an electromagnetic inductive action.

According to the charging unit for the sphygmomanometer configured as above, the secondary battery inside the sphygmomanometer can be charged with a simple operation and with high reliability.

According to one or more embodiments of the present invention, the bag-shaped cover body takes a form of a tubular shape. The positioning unit is formed from a shaft member to which the tubular bag-shaped cover body can be inserted. According to the charging unit for the sphygmomanometer configured as above, the power reception unit is arranged at a position capable of receiving power from the power transmission unit at the same time as when the bag-shaped cover body is inserted to the position unit, and hence the secondary battery can be charged with a simpler operation. Moreover, the storage state of the sphygmomanometer can be improved and the accuracy in the measurement of the blood pressure can be enhanced.

According to one or more embodiments of the present invention, the positioning unit is formed from a clip member capable of sandwiching the bag-shaped cover body. According to the charging unit for the sphygmomanometer configured as above, the charging device can be configured easily and compactly.

According to one or more embodiments of the present invention, the power reception unit and the power transmission unit have a communication function for enabling wireless communication between the sphygmomanometer and the charging device. According to the charging unit of the sphygmomanometer configured as above, information can be transmitted and received between the sphygmomanometer and the charging device while charging the secondary battery.

According to one or more embodiments of the present invention, the charging device further includes a memory for storing information communicated from the power reception unit toward the power transmission unit. According to the charging unit for the sphygmomanometer configured as above, the information such as measurement results can be managed on the charging device side.

As described above, according to one or more embodiments of the present invention, a sphygmomanometer in which the secondary battery can be charged through a simple operation and with high reliability, and a charging unit for the sphygmomanometer can be provided.

DETAILED DESCRIPTION OF INVENTION

Figure 1:
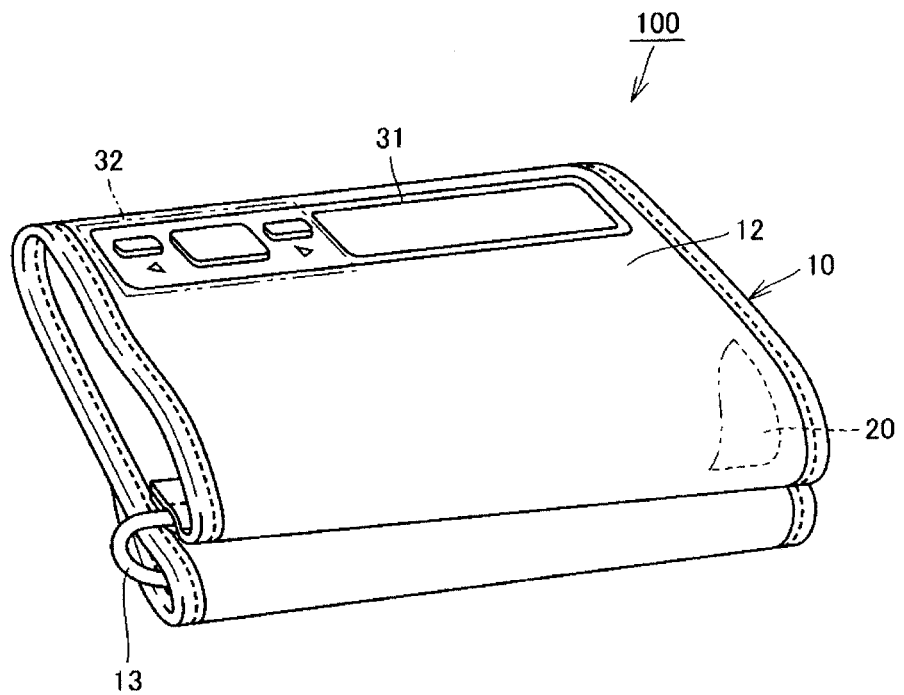
FIG. 1 is a perspective view showing an outer appearance of a sphygmomanometer according to a first embodiment of the present invention.

Embodiments of the present invention will be described with reference to the drawings. In the drawings referenced below, the same numbers are denoted for the same or corresponding members.

First Embodiment

FIG. 1 is a perspective view showing an outer appearance of a sphygmomanometer according to a first embodiment of the present invention. With reference to FIG. 1, a sphygmomanometer 100 is an automatic sphygmomanometer that is driven upon receiving power supply from a battery. The sphygmomanometer 100 includes a cuff 10. The sphygmomanometer 100 is an upper arm type sphygmomanometer in which the cuff 10 is attached to the upper arm of a subject.

The cuff 10 includes a display unit 31 for displaying various information including blood pressure measurement results, and an operation unit 32 operated to input various instructions for measurement. The display unit 31 visually displays the measurement result of the blood pressure value, the measurement result of the pulse rate, or the like using numerical values, graphs, and the like. A liquid crystal panel, or the like are used for the display unit 31. The operation unit 32 includes various types of buttons such as a power button and a measurement start button, a scroll button for switching the screen of the display unit 31, and the like.

The cuff 10 has a band-shaped outer appearance, and is wrapped around the periphery of the upper arm of the subject in a tubular form at the time of blood pressure measurement. The cuff 10 includes an air bag 20 for compressing the upper arm, and a bag-shaped cover body 12 for wrapping around and attaching the air bag 20 to the upper arm. The air bag 20 is accommodated in a space arranged inside the bag-shaped cover body 12.

Figure 2:
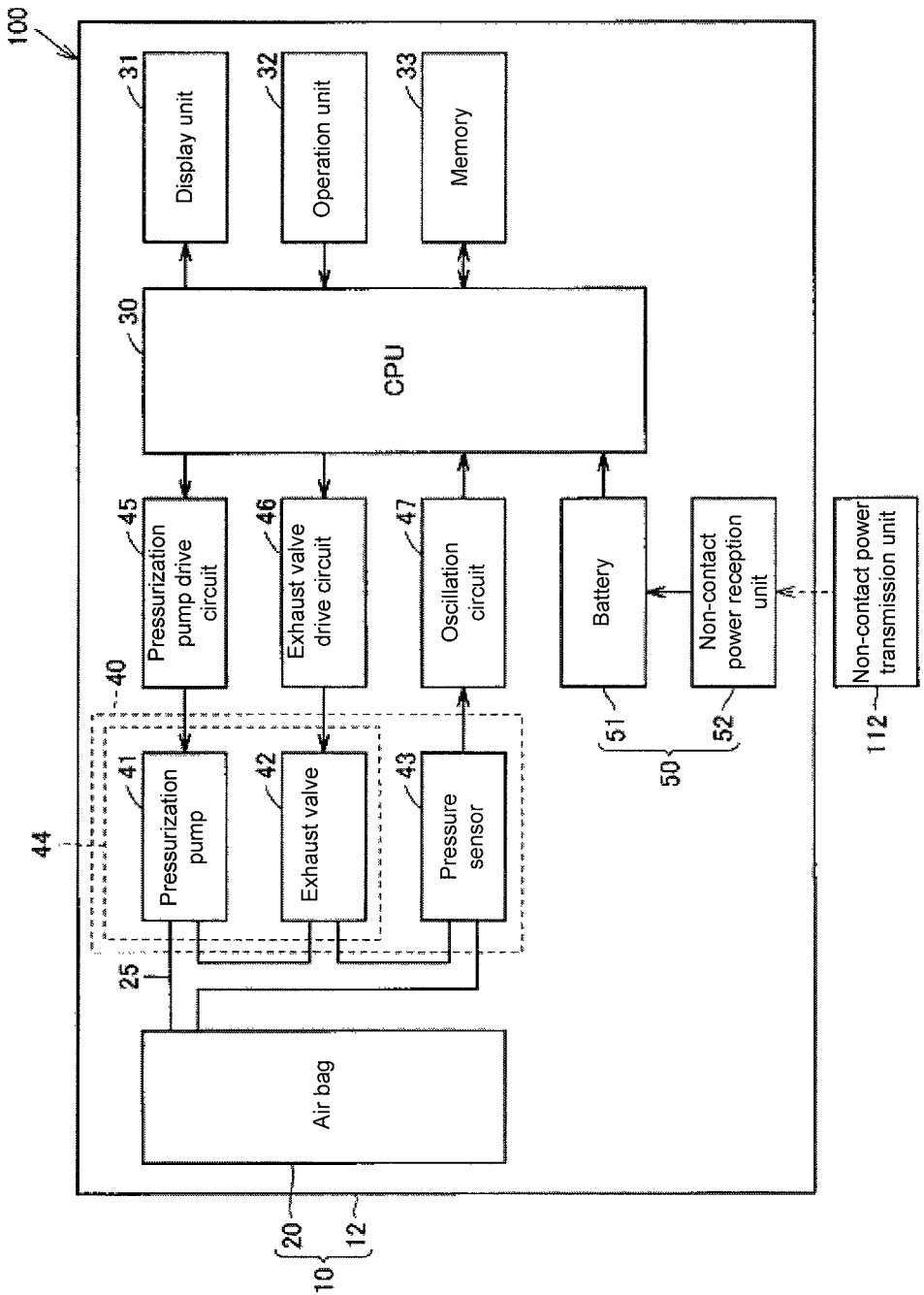
FIG. 2 is a function block diagram showing a configuration of the sphygmomanometer in FIG. 1.

FIG. 2 is a function block diagram showing a configuration of the sphygmomanometer in FIG. 1. With reference to FIG. 1 and FIG. 2, the cuff 10 includes a blood pressure measurement air system component 40 for supplying or discharging air to and from the air bag 20. The air bag 20 and the blood pressure measurement air system component 40 are connected by an air tube 25 serving as a fluid tube.

The blood pressure measurement air system component 40 includes a pressurization pump 41 and an exhaust valve 42 that are an expansion and contraction mechanism for expanding and contracting the air bag 20, and a pressure sensor 43 as a pressure detection means for detecting the pressure in the air bag 20. The cuff 10 includes a pressurization pump drive circuit 45, an exhaust valve drive circuit 46, and an oscillation circuit 47 in relation to the blood pressure measurement air system component 40.

The cuff 10 also includes a CPU (Central Processing Unit) 30 for controlling and monitoring each unit in a concentrated manner, and a memory 33 for storing programs for causing the CPU 30 to perform a predetermined operation and various types of information such as measured blood pressure value. The CPU 30 also functions as a blood pressure value calculation means for calculating the blood pressure value.

The pressure sensor 43 detects the pressure in the air bag 20 (hereinafter referred to as "cuff pressure") and outputs a signal corresponding to the detected pressure to the oscillation circuit 47. The pressurization pump 41 supplies air to the air bag 20. The exhaust valve 42 opens and closes to maintain the pressure in the air bag 20 or to discharge the air in the air bag 20. The oscillation circuit 47 outputs a signal of an oscillating frequency corresponding to the output value of the pressure sensor 43 to the CPU 30. The pressurization pump drive circuit 45 controls the drive of the pressurization pump 41 based on a control signal provided from the CPU 30. The exhaust valve drive circuit 46 performs the open/close control of the exhaust valve 42 based on a control signal provided from the CPU 30.

The cuff 10 further includes a power supply unit 50 for supplying power to each function block such as the expansion and contraction mechanism 44 and the CPU 30. The power supply unit 50 includes a battery 51 configured by a chargeable secondary battery, and a non-contact power reception unit 52 for charging the battery 51.

Figure 3:
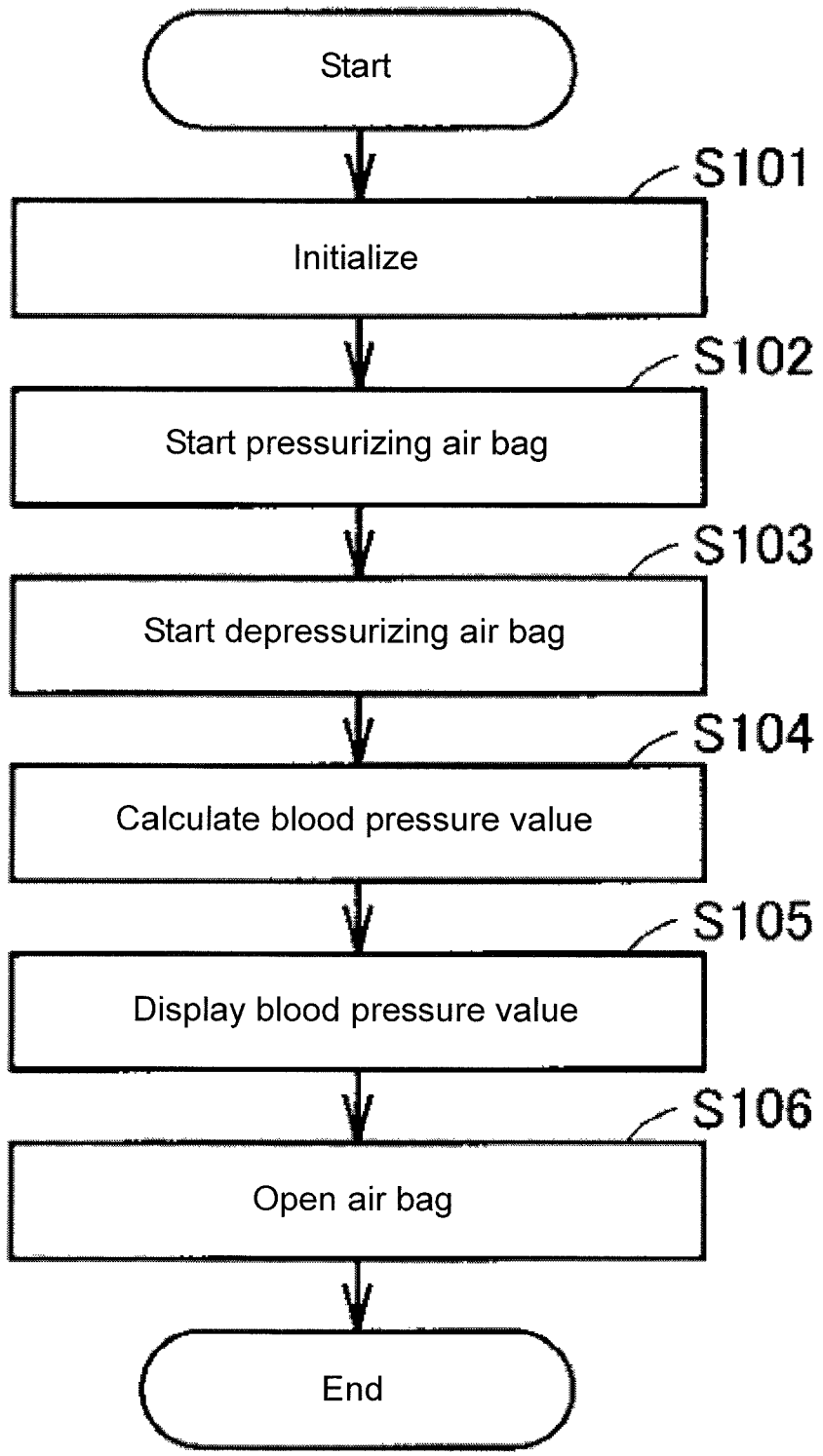
FIG. 3 is a flowchart showing the flow of the blood pressure measurement process of the sphygmomanometer in FIG. 1.

The flow of the blood pressure measurement process in the sphygmomanometer 100 will now be described. FIG. 3 is a flowchart showing the flow of the blood pressure measurement process of the sphygmomanometer in FIG. 1. The program that complies with the flowchart is stored in advance in the memory 33 shown in FIG. 2, where the CPU 30 reads out the program from the memory 33 and executes the program to perform the blood pressure measurement process.

With reference to FIG. 2 and FIG. 3, when the subject operates the operation button of the operation unit 32 of the sphygmomanometer 100 to turn ON the power supply, the initialization of the sphygmomanometer 100 is performed (step S101). When in a measurable state, the CPU 30 starts to drive the pressurization pump 41 and gradually raises the cuff pressure of the air bag 20 (step S102). When the cuff pressure reaches a predetermined level necessary for the blood pressure measurement in the process of gradually pressurizing the cuff pressure, the CPU 30 stops the pressurization pump 41. The CPU 30 then gradually opens the exhaust valve 42, which was closed, to gradually exhaust the air of the air bag 20 and gradually depressurize the cuff pressure (step S103). The cuff pressure is detected in the process of depressurizing the cuff pressure at very slow speed.

The CPU 30 then calculates the systolic blood pressure value (highest blood pressure value) and the diastolic blood pressure value (lowest blood pressure value) through the known procedure (step S104). Specifically, the CPU 30 extracts pulse wave information based on the oscillating frequency obtained from the oscillation circuit 47 in the process of gradually depressurizing the cuff pressure. The blood pressure value is calculated from the extracted pulse wave information. After the blood pressure value is calculated in step S104, the CPU 30 displays the calculated blood pressure value on the display unit 31 (step S105).

Thereafter, the CPU 30 opens the air bag 20 to completely exhaust the air in the air bag 20 (step S106), and waits for a command to turn OFF the power supply by the subject to terminate the operation. The measurement method described above is based on the so-called depressurization measurement method in which the pulse wave is detected at the time of depressurization of the air bag 20, but the so-called pressurization measurement method in which the pulse wave is detected at the time of pressurization of the air bag 20 may, of course, be adopted.

Figure 4:
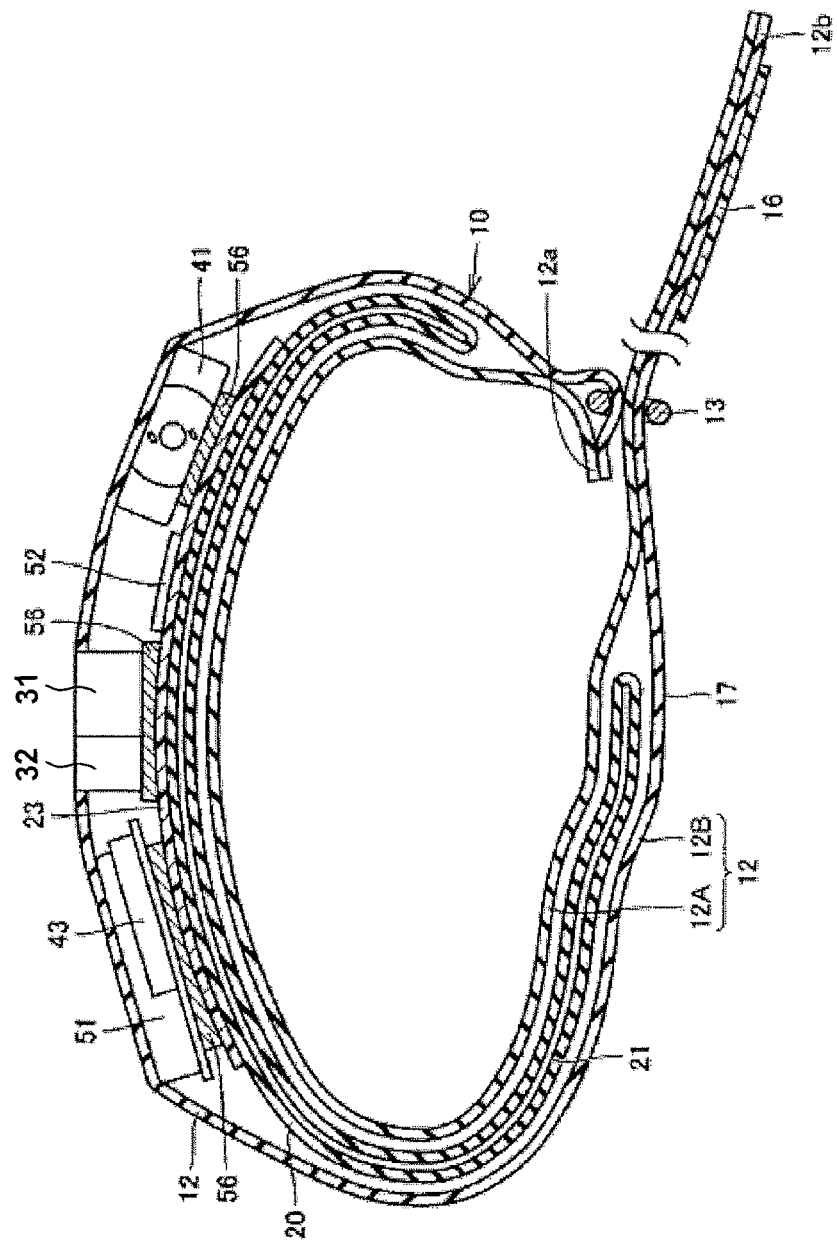
FIG. 4 is a cross-sectional view showing the sphygmomanometer in FIG. 1.

A more specific structure of the sphygmomanometer 100 will now be described. FIG. 4 is a cross-sectional view showing the sphygmomanometer in FIG. 1.

With reference to FIG. 4, the air bag 20 has a band shape in the developed state. The air bag 20 is suitably a bag shaped member formed using a resin sheet. An expansion and contraction space 21 is formed inside the air bag 20. The air tube 25 in FIG. 2 communicates to the expansion and contraction space 21. The air bag 20 expands and contracts when air is supplied to and exhausted from the expansion and contraction space 21. The air bag 20 is accommodated inside the bag shaped cover body 12.

The material of the resin sheet for forming the air bag 20 may be any that has stretchability and in which air does not leak out from the expansion and contraction space 21. From such a standpoint, ethylene-vinyl acetate copolymer (EVA), flexible polyvinyl chloride (PVC), polyurethane (PU), polyamide (PA), raw rubber, and the like can be used as a suitable material of the resin sheet.

The bag shaped cover body 12 is formed to a band shape including a longitudinal direction and a short direction in the developed state. The bag shaped cover body 12 includes one end 12a and another end 12b at both ends in the longitudinal direction. The bag shaped cover body 12 is wrapped around the upper arm so as to curve along the longitudinal direction when attached to the upper arm.

The bag shaped cover body 12, includes an inner cover member 12A that configures the inner exterior package positioned on the upper arm side in the attached state, and an outer cover member 12B that configures the outer exterior package arranged on the side opposite to the upper arm with the air bag 20 in between. The inner cover member 12A and the outer cover member 12B are overlapped, and the peripheral edge is joined using a bias tape, and the like.

The bag shaped cover body 12 is suitably formed by a fabric made of synthetic fiber such as polyamide (PA) or polyester. The inner cover member 12A is suitably configured by a member that excels in stretchability, and the outer cover member 12B is suitably configured by a member that lacks in stretchability than the inner cover member 12A.

A ring member 13 is attached to the one end 12a of the bag shaped cover body 12, and a portion of the bag shaped cover body 12 on the other end 12b side is inserted to the ring member 13. A surface fastener 16 is arranged on the outer peripheral surface of the portion closer to the other end 12b than the portion inserted to the ring member 13 of the bag shaped cover body 12, and a surface fastener 17 is arranged on the outer peripheral surface of the portion closer to the one end 12a than the portion inserted to the ring member 13 of the bag shaped cover body 12. The surface fastener 16 and the surface fastener 17 engage when the portion on the other end 12b side of the bag shaped cover body 12 is inserted to the ring member 13 and folded back at the ring member 13 as the base point. The cuff 10 is thereby wrapped around the upper arm, and fixed thereto.

Figure 5:
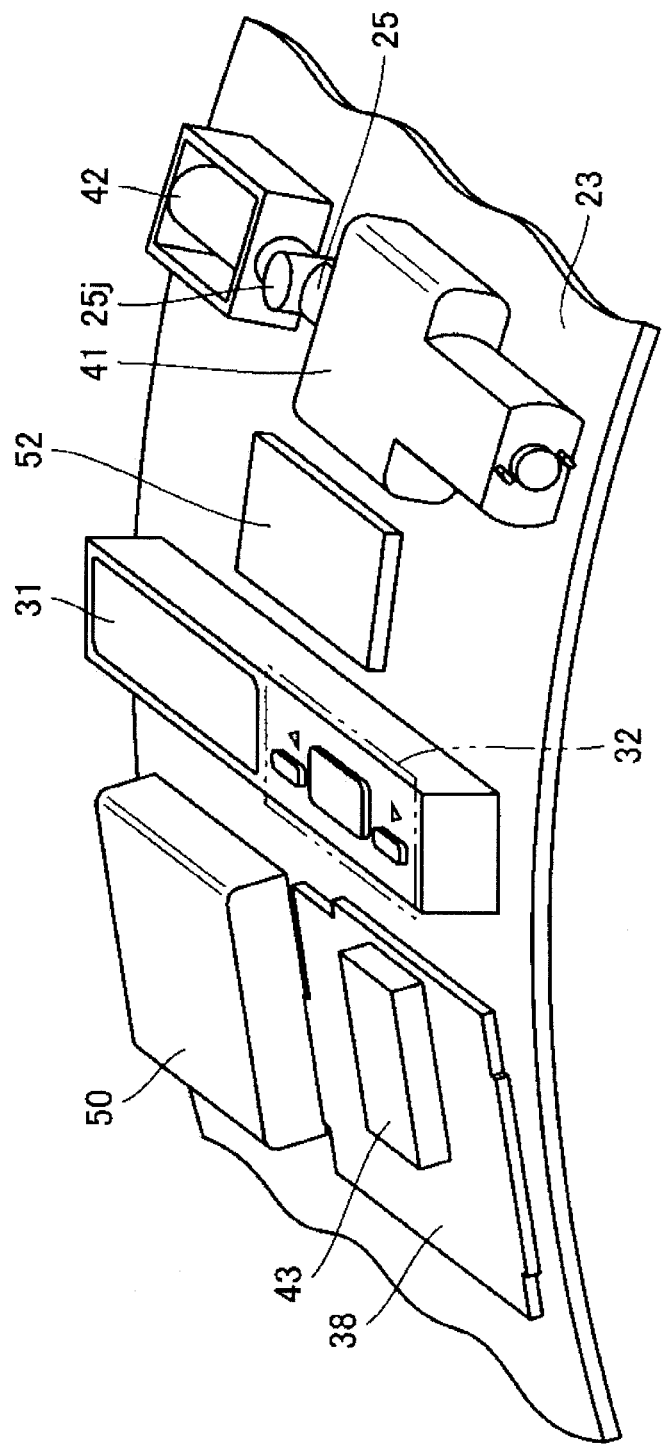
FIG. 5 is a perspective view showing an inner structure of the sphygmomanometer in FIG. 1.

FIG. 5 is a perspective view showing an inner structure of the sphygmomanometer in FIG. 1. With reference to FIG. 4 and FIG. 5, a curler 23 is accommodated inside the bag shaped cover body 12. The curler 23 has flexibility, and is formed by being curved to an arcuate shape along the surface of the upper arm. The curler 23 is arranged overlapping the outer side of the air bag 20. The curler 23 is formed with a resin member such as polypropylene (PP).

The power supply unit 50, that is, the battery 51 and the non-contact power reception unit 52 are accommodated inside the bag shaped cover body 12. The type of battery 51 is not particularly limited as long as it is a chargeable secondary battery, and may be a nickel hydride battery, lithium ion battery, or nickel-cadmium battery. The non-contact power reception unit 52 is connected to the battery 51 by wiring (not shown). The non-contact power reception unit 52 is arranged between the outer cover member 12B and the curler 23. In the present embodiment, the non-contact power reception unit 52 is fixed with respect to the curler 23. The non-contact power reception unit 52 is arranged near the display unit 31 and the operation unit 32, where the position of the non-contact power reception unit 52 can be recognized as the display unit 31 and the operation unit 32 serve as a mark in the present embodiment.

The non-contact power reception unit 52 may be arranged at the position that does not overlap the air bag 20 in the bag shaped cover body 12 (e.g., zone between the air bag 20 and the one end 12a of the bag shaped cover body 12). According to such a configuration, the presence of the non-contact power reception unit 52 suppresses the influence on the expansion and contraction process of the air bag 20 small, and maintains the measurement accuracy of the blood pressure value high.

In the present embodiment, the blood pressure measurement air system component 40 in FIG. 2, various types of electric circuits such as the pressurization pump drive circuit 45, the exhaust valve drive circuit 46 and the oscillation circuit 47, the CPU 30 and the memory 33, and the display unit 31 and the operation unit 32 are accommodated inside the bag shaped cover body 12. In other words, the sphygmomanometer 100 in the present embodiment is an integrated sphygmomanometer having a mode in which all the electronic components are accommodated in the bag shaped cover body 12 of the cuff 10.

The pressurization pump 41, the exhaust valve 42, the pressure sensor 43, the air tube 25 including an air joint 25j, the circuit substrate 38 formed with various types of electric circuits, the battery 51, and the display unit 31 and the operation unit 32 are mounted on the outer peripheral surface of the curler 23 (i.e., main surface on the side opposite to the main surface (inner peripheral surface) on the side facing the air bag 20 of the curler 23) in the bag shaped cover body 12.

An adhesive sheet 56 serving as a fixing member is used to mount the components on the curler 23. The curler 23 is formed to a curved shape to lie along the upper arm, and hence the adhesive sheet in which a member having cushion property such as a sponge member, rubber member, or resin member is used as the base material, and the adhesive layer is arranged on both surfaces thereof is suitably used for the adhesive sheet 56. Through the use of such an adhesive sheet 56, the base material portion of the adhesive sheet 56 deforms thereby filling the gap between the curler 23 and the component, whereby the component can be more stably fixed to the curler 23.

In the present embodiment, the curler 23 is arranged only as a base for mounting the configuring components of the sphygmomanometer 100, but the curler 23 may function as a curved elastic plate for biasing the air bag 20 toward the upper arm by being extended in the longitudinal direction of the bag shaped cover body 12 and formed to a cylindrical shape.

The charging method of the sphygmomanometer 100 will now be described in detail. With reference to FIG. 2, the battery 51 is charged through the non-contact charging method in the sphygmomanometer 100 in the present embodiment. The non-contact charging is realized by the non-contact power reception unit 52 and the non-contact power transmission unit 112, where the power is transmitted in a non-contact manner from the non-contact power transmission unit 112 to the non-contact power reception unit 52 using the electromagnetic inductive action.

Figure 6A:
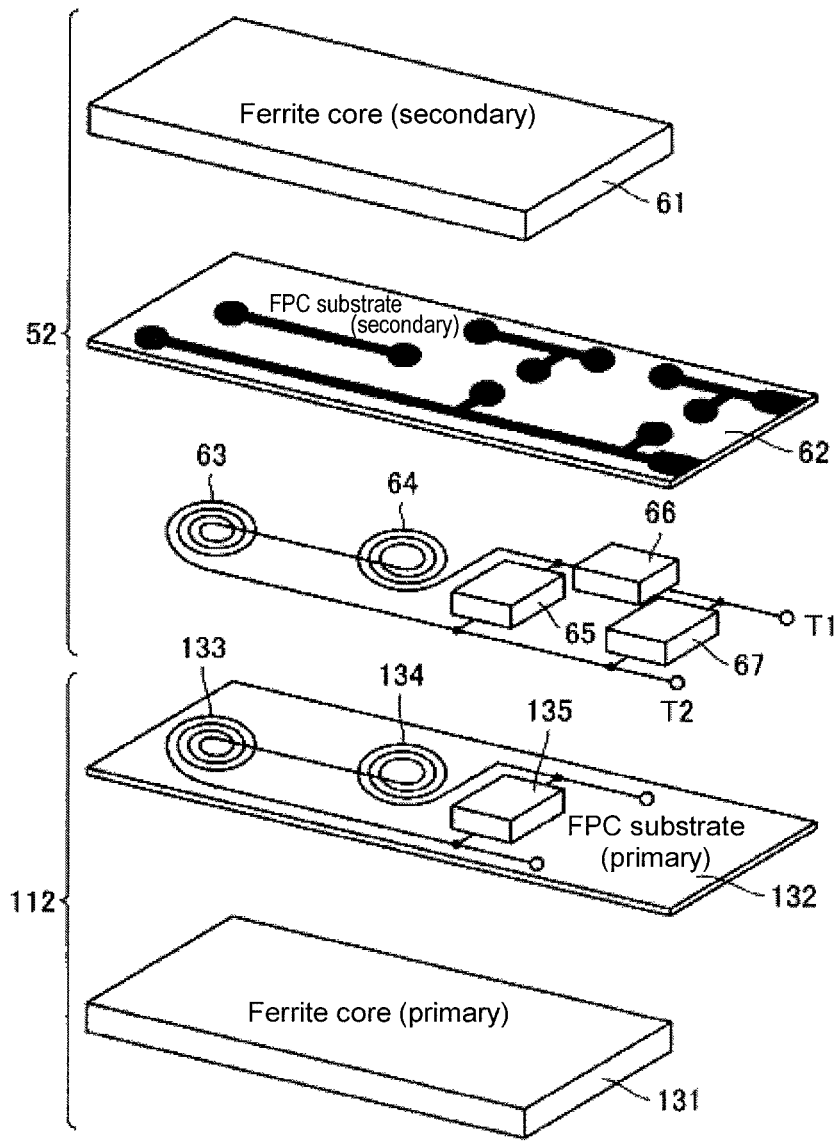
FIG. 6A is a perspective view showing a specific configuration of the non-contact power transmission unit and the non-contact power reception unit in FIG. 2, and is a view showing the device configuration of the non-contact power transmission unit and the non-contact power reception unit.
Figure 6B:
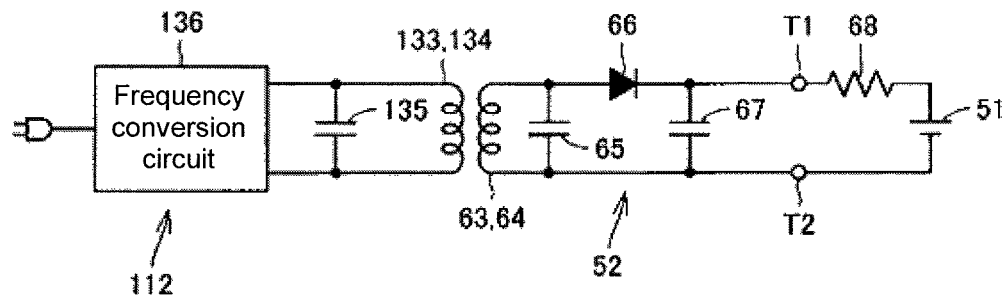
FIG. 6B is a perspective view showing a specific configuration of the non-contact power transmission unit and the non-contact power reception unit in FIG. 2, and is a view showing the circuit configuration of the non-contact power transmission unit and the non-contact power reception unit.

FIG. 6A is a perspective view showing a specific configuration of the non-contact power transmission unit and the non-contact power reception unit in FIG. 2, and is a view showing the device configuration of the non-contact power transmission unit and the non-contact power reception unit. FIG. 6B is a perspective view showing a specific configuration of the non-contact power transmission unit and the non-contact power reception unit in FIG. 2, and is a view showing the circuit configuration of the non-contact power transmission unit and the non-contact power reception unit.

With reference to FIG. 6A and FIG. 6B, the non-contact power transmission unit 112 includes a primary side ferrite core 131 of soft magnetic property, and a primary side FPC (Flexible Printed Circuit) substrate 132. A pair of coils 133, 134 and a resonance capacitor 135 are arranged on the primary side FPC substrate 132. The pair of coils 133, 134 are wounded so that the direction of the magnetic flux generated by the coils becomes opposite to each other, and are connected in series. The pair of coils 133, 134 and the resonance capacitor 135 are connected in parallel with respect to the output of a frequency conversion circuit 136 configured by a switching power supply.

The non-contact power reception unit 52 includes a secondary side ferrite core 61 of soft magnetic property, and a secondary side FPC substrate 62. A pair of coils 63, 64, a resonance capacitor 65, a rectifier diode 66, and a smoothing condenser 67 are arranged on the secondary side FPC substrate 62. The coil 63 and the coil 64 are arranged to face the coil 133 and the coil 134, respectively, at the time of charging. The coils 63, 64 are wounded so that the direction of the current generated due to the change in the magnetic flux generated by the coils 133, 134 is the same direction, and are connected in series. The coils 63, 64 connected in series are connected in parallel with the resonance capacitor 65. The rectifier diode 66 and the smoothing condenser 67 are connected in series, and the smoothing condenser 67 is connected in parallel with the resonance capacitor 65. The output terminals T1, T2 at both ends of the smoothing condenser 67 are connected to the battery 51 through a voltage adjuster 68.

In the present embodiment, the non-contact power reception unit 52 can be easily laid along the shape of the bag shaped cover body 12 attached to the upper arm of the subject by using the secondary side FPC substrate 62 having flexibility.

The device configuration and the circuit configuration of the non-contact power transmission unit 112 and the non-contact power reception unit 52 described above are examples, and may be appropriately changed. For instance, the substrate for forming the coils and the various types of circuits is not limited to the FPC substrate, and may be a general substrate that does not have flexibility.

Figure 7:
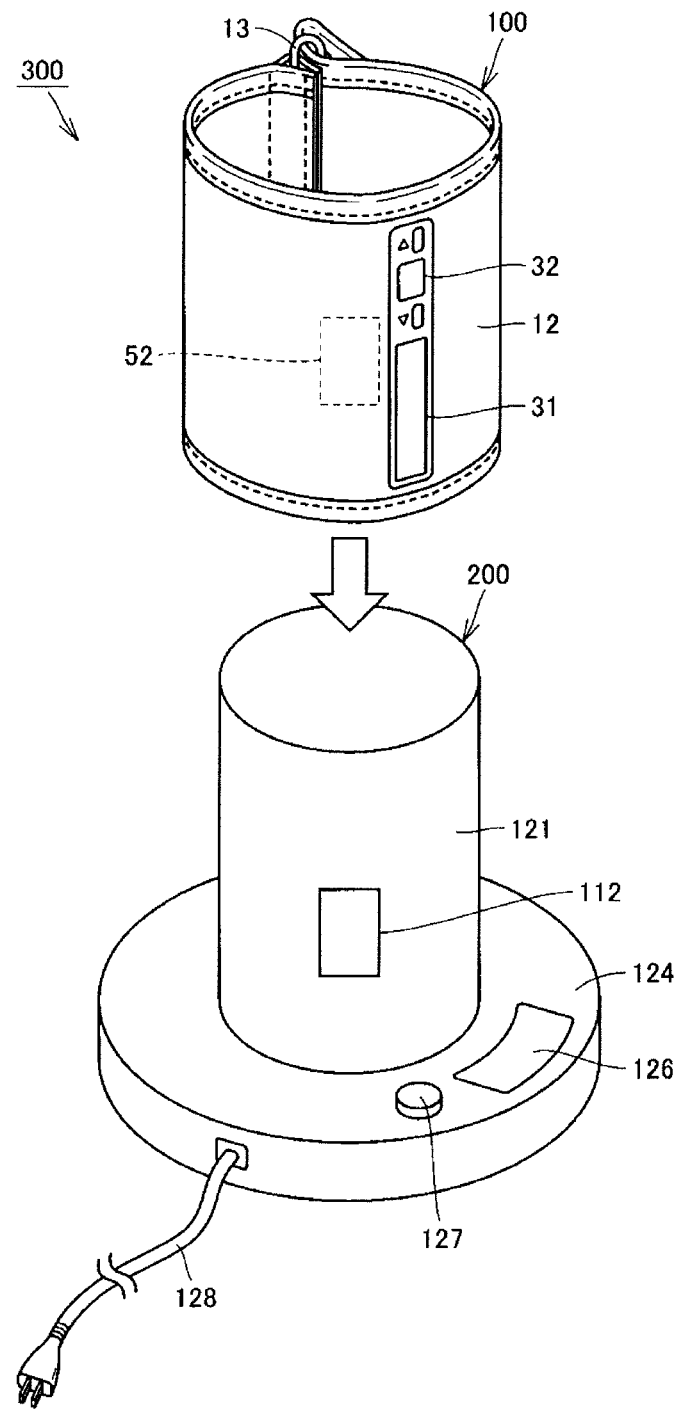
FIG. 7 is a perspective view showing a charging unit for a sphygmomanometer in the first embodiment of the present invention.
Figure 8:
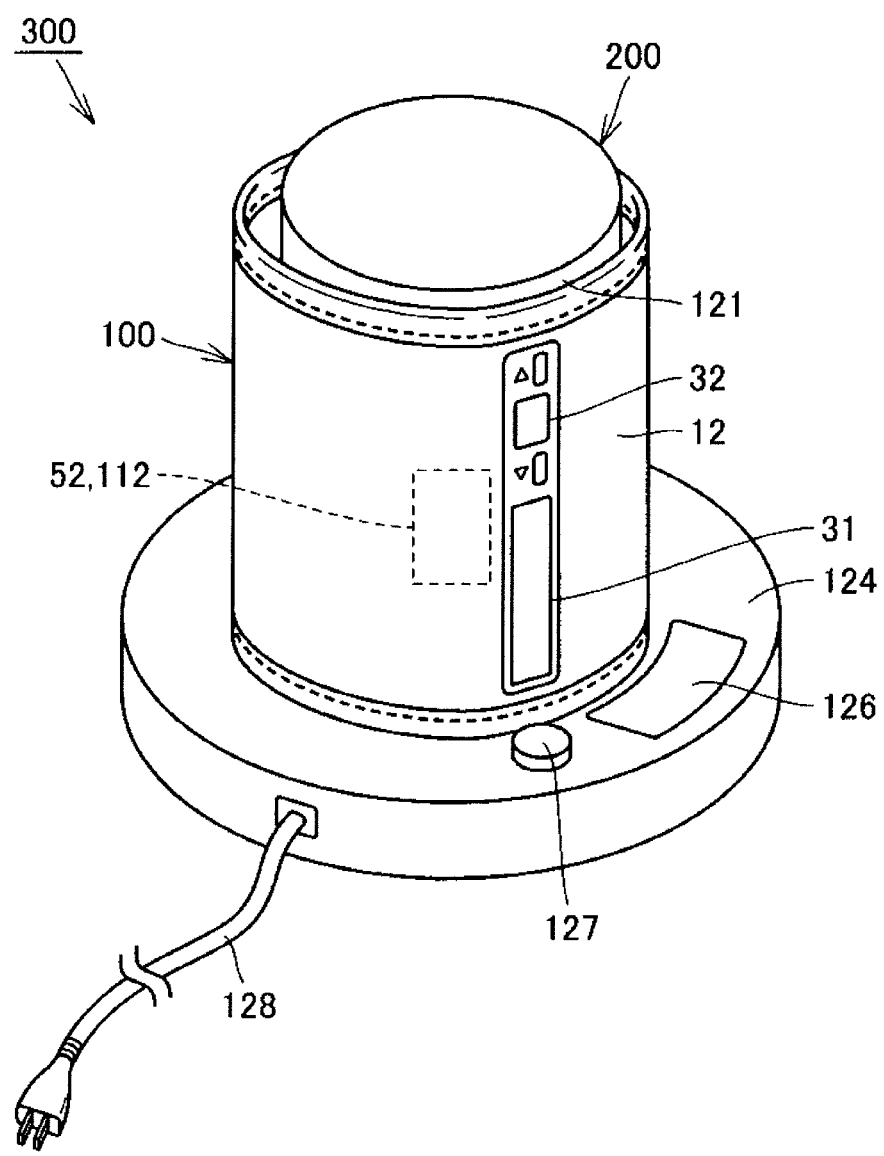
FIG. 8 is a perspective view showing a state in which the sphygmomanometer is set in the charging device in the charging unit for the sphygmomanometer in FIG. 7.

FIG. 7 is a perspective view showing a charging unit for sphygmomanometer in the first embodiment of the present invention. FIG. 8 is a perspective view showing a state in which the sphygmomanometer is set in the charging device in the charging unit for the sphygmomanometer in FIG. 7.

With reference to FIG. 7 and FIG. 8, a charging unit 300 for the sphygmomanometer according to the present embodiment is configured by the sphygmomanometer 100 including the non-contact power reception unit 52 and a charging device 200, including the non-contact power transmission unit 112, for charging the battery 51 of the sphygmomanometer 100.

The charging device 200 is formed to include a base 124 and a shaft 121. The base 124 is the portion mounted at the installing location of the charging device 200 such as the top of the desk. The shaft 121 has a circular column shape extending from the base 124, and has a shape capable of receiving the bag shaped cover body 12 of tubular shape. The non-contact power transmission unit 112 is arranged at the outer peripheral surface of the shaft 121. The bag shaped cover body 12 is inserted to the shaft 121 while aligning the positions of the display unit 31 and the operation unit 32, and the non-contact power transmission unit 112, so that the non-contact power reception unit 52 and the non-contact power transmission unit 112 are positioned to face each other.

If the non-contact power reception unit 52 is not arranged in the vicinity of the display unit 31 and the operation unit 32, a mark indicating the position of the non-contact power reception unit 52 may be separately provided on the surface of the bag shaped cover body 12.

The charging device 200 includes a display unit 126, an operation unit 127, and a power supply cord 128. The display unit 126 visually displays the start and end of the charging of the battery 51, and the like. The operation unit 127 includes a charging start button for starting the charging. The power supply cord 128 introduces the alternating current (AC) power to the charging device 200 by being inserted to an outlet at the time of charging. An AC adapter for converting the introduced AC power to the direct current (DC) power for charging the battery 51 is incorporated in the charging device 200.

In the present embodiment, the battery 51 of the sphygmomanometer 100 is charged through the non-contact charging method. According to such configuration, the connection terminal, to which the plug from the charger is to be inserted at the time of charging, does not need to be arranged at the sphygmomanometer 100. As a result, the housing for providing the connection terminal is unnecessary, the structure in which the battery 51 is accommodated inside the bag shaped cover body 12, as shown in FIG. 4 and FIG. 5, can be adopted, and the sphygmomanometer 100 can be miniaturized. Because the connection terminal does not need to be arranged at the sphygmomanometer 100, there is no longer the concern for lowering of the charging efficiency due to degradation of the terminal, and the drip-proof, dust-proof performance of the product can be enhanced.

Furthermore, in the present embodiment, the user of the sphygmomanometer 100 can obtain the state to start the charging by simply inserting the tubular bag shaped cover body 12 into the shaft 121 of the charging device 200. Thus, the user can set the sphygmomanometer 100 with respect to the charging device 200 as if cleaning up the sphygmomanometer 100 after use without particularly feeling the work for charging.

Furthermore, the storage state of the cuff 10 can be enhanced and the cuff 10 can be maintained clean because the cuff 10 is stored in a state inserted to the shaft 121 as shown in FIG. 8. Thus, the measurement accuracy of the blood pressure value by the sphygmomanometer 100 can be enhanced. In particular, in the sphygmomanometer 100 according to the present embodiment, the cuff 10 easily deforms when roughly handled since the curler 23 is not arranged as a curved elastic plate for biasing the air bag 20 toward the upper arm. Therefore, the effect in which the storage state of the cuff 10 enhances can be more effectively obtained.

The sphygmomanometer in the first embodiment of the present invention includes the air bag 20, which is supplied with air serving as fluid and which serves as a fluid bag that expands and contracts, the bag shaped cover body 12 for accommodating the air bag 20 and attaching the air bag 20 to the upper arm that is a site to be measured, the expansion and contraction mechanism 44 for expanding and contracting the air bag 20, and the power supply unit 50 arranged in the bag shaped cover body 12. The power supply unit 50 includes the battery 51 serving as the secondary battery for supplying driving power to the expansion and contraction mechanism 44, and the non-contact power reception unit 52 serving as the power reception unit for receiving power to charge the battery 51. The non-contact power reception unit 52 is supplied with power through the electromagnetic inductive action from the non-contact power transmission unit 112 serving as the power transmission unit arranged in a non-contact state from the non-contact power reception unit 52.

The charging unit 300 for the sphygmomanometer according to the first embodiment of the present invention includes the sphygmomanometer 100, and the charging device 200 for charging the battery 51. The charging device 200 includes the shaft 121 serving as a positioning unit positioned with respect to the bag shaped cover body 12, and the non-contact power transmission unit 112, arranged to face the non-contact power reception unit 52 in the non-contact state when the shaft 121 is positioned with respect to the bag shaped cover body 12, and capable of supplying power to the non-contact power reception unit 52 through the electromagnetic inductive action.

According to the sphygmomanometer and the charging unit for the sphygmomanometer of the first embodiment of the present invention configured as above, the battery 51 can be charged through a simple task and with high reliability.

The upper arm type sphygmomanometer 100 in which the cuff 10 is attached to the upper arm of the subject has been described in the present embodiment, but the present invention is not limited thereto, and may be applied to a wrist type sphygmomanometer.

Second Embodiment

In the present embodiment, another charging method of the sphygmomanometer 100 in the first embodiment, and various variants of the charging unit 300 for the sphygmomanometer will be described. The description on the redundant structure will not be repeated below.

Figure 9:
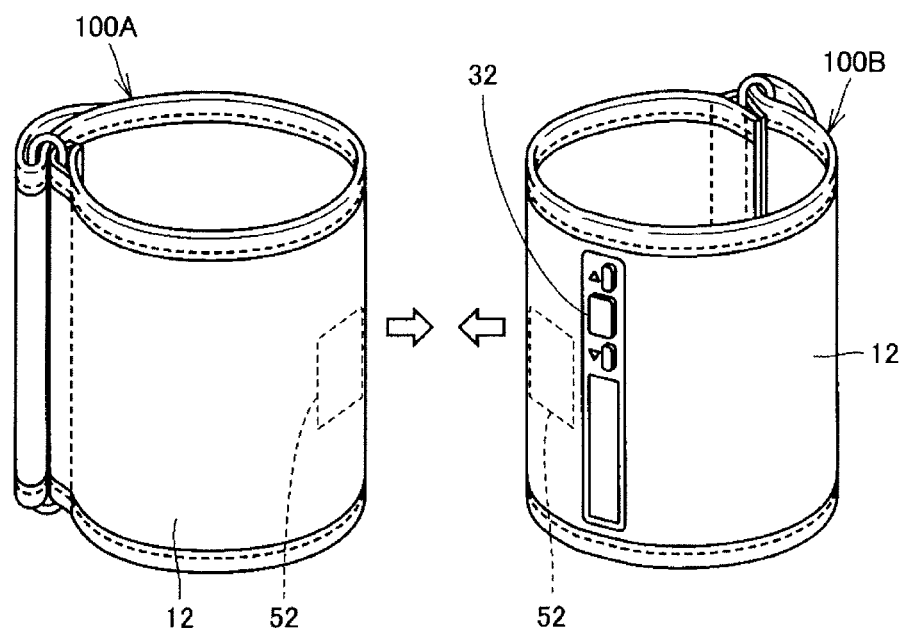
FIG. 9 is a perspective view showing another charging method of the sphygmomanometer in FIG. 1.

FIG. 9 is a perspective view showing another charging method of the sphygmomanometer in FIG. 1. With reference to FIG. 9, a plurality of sphygmomanometers 100A, 100B are prepared in this charging method. The non-contact power reception unit 52 arranged in each sphygmomanometer 100 has a power transmission function (the same function as non-contact power transmission unit 112) that enables transmission and reception of power between the sphygmomanometer 100A and the sphygmomanometer 100B.

In other words, the non-contact power reception unit 52 arranged in one of the sphygmomanometer 100A or the sphygmomanometer 100B is started as the power reception side and the non-contact power reception unit 52 arranged in the other one of the sphygmomanometer 100A or the sphygmomanometer 100B is started as the power transmission side by the operation of the operation unit 32. The power of the battery 51 arranged in one of the sphygmomanometer 100A or the sphygmomanometer 100B is transmitted to the battery 51 arranged in the other one of the sphygmomanometer 100A or the sphygmomanometer 100B by bringing the non-contact power reception units 52 arranged in the sphygmomanometer 100A and the sphygmomanometer 100B close.

With such configuration, if a plurality of sphygmomanometers 100 is prepared, the respective lack of power can be compensated, and the battery 51 can be charged even in areas where power supply cannot be ensured.

Figure 10:
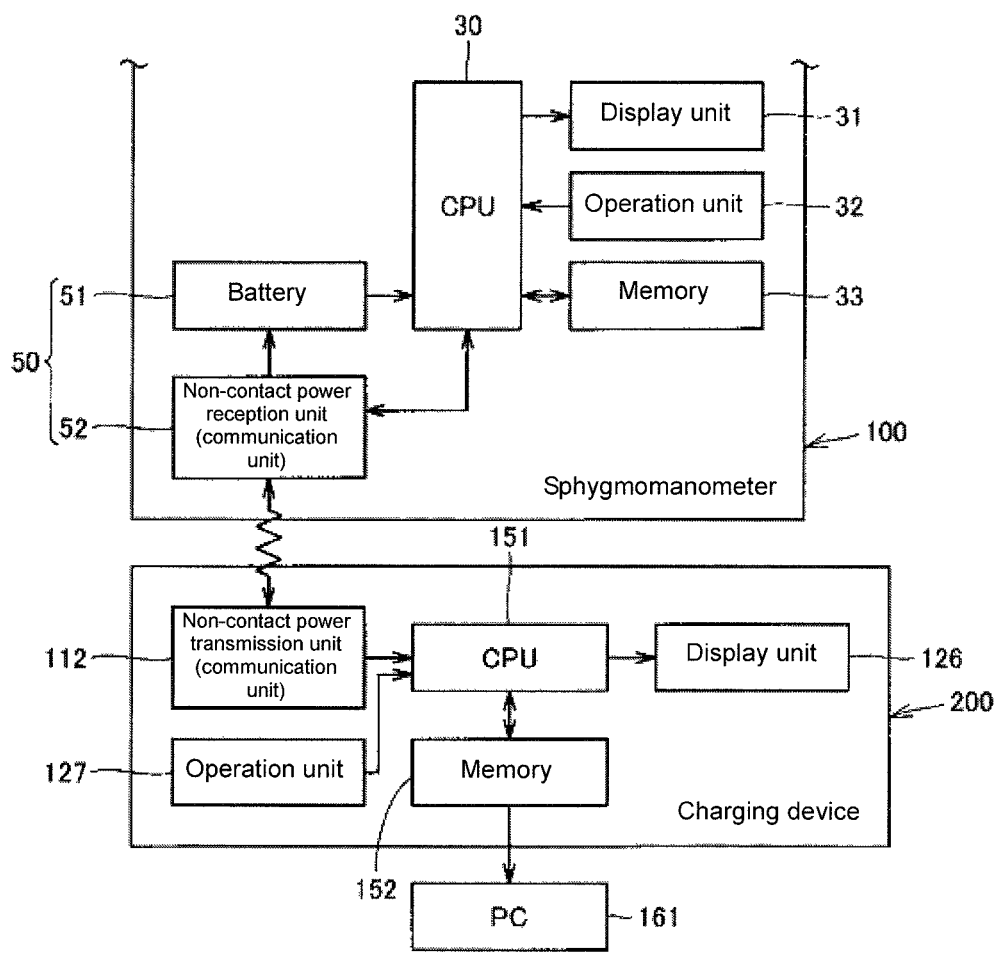
FIG. 10 is a function block diagram showing a first variant of the charging unit for the sphygmomanometer in FIG. 7.

FIG. 10 is a function block diagram showing a first variant of the charging unit for the sphygmomanometer in FIG. 7. In the figure, one part of the function block of the sphygmomanometer 100 shown in FIG. 2 is not described.

With reference to FIG. 10, in the present variant, the non-contact power reception unit 52 and the non-contact power transmission unit 112 transmit and receive power between the sphygmomanometer 100 and the charging device 200, and also function as a communication unit to exchange information through wireless communication using change in magnetic force as a medium. That is, the coil incorporated in the non-contact power reception unit 52 and the non-contact power transmission unit 112 is used as a transmission coil for emitting the change in magnetic force and a reception coil for receiving the change in magnetic force.

The charging device 200 includes a CPU 151 and a memory 152. The information regarding the measurement result stored in the memory 33 of the sphygmomanometer 100 is transmitted to the charging device 200 through the wireless communication between the non-contact power reception unit 52 and the non-contact power transmission unit 112. The CPU 151 stores the information transmitted by the sphygmomanometer 100 in the memory 152. An external terminal 161 of the PC (Personal Computer) or the like is connected to the charging device 200, and the information stored in the memory 152 is further transferred to the external terminal 161.

According to such a configuration, the information can be transferred from the sphygmomanometer 100 to the charging device 200 while charging the battery 51 without newly arranging a wireless device. Thus, the measurement results can be centrally managed in the charging device 200 and the external terminal 161, thereby reducing the load of information management on the user.

Figure 11:
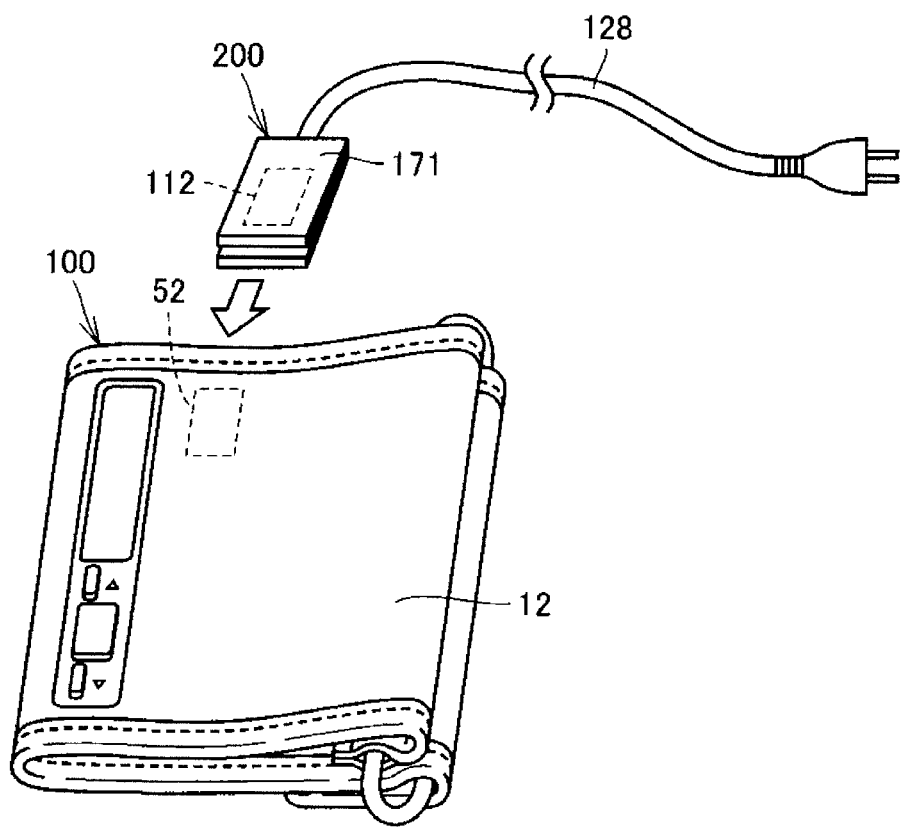
FIG. 11 is a perspective view showing a second variant of the charging unit for the sphygmomanometer in FIG. 7.

FIG. 11 is a perspective view showing a second variant of the charging unit for the sphygmomanometer in FIG. 7. With reference to FIG. 11, in the sphygmomanometer 100 according to the present variant, the non-contact power reception unit 52 is arranged near the peripheral edge extending in the longitudinal direction of the bag shaped cover body 12.

The charging device 200 in the present variant includes a clip 171 serving as the positioning unit, and the non-contact power transmission unit 112 arranged at the clip 171. The clip 171 is configured to have a clip structure capable of sandwiching the bag shaped cover body 12. The non-contact power transmission unit 112 is arranged at a position to face the non-contact power reception unit 52 with the peripheral edge of the bag shaped cover body 12 sandwiched by the clip 171. According to such configuration, the charging device 200 can be configured simply and compactly.

According to the sphygmomanometer and the charging unit for the sphygmomanometer according to the second embodiment of the present invention configured as above, effects similar to the effects described in the first embodiment can be obtained.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

DESCRIPTION OF REFERENCE NUMERALS 12 bag shaped cover body
20 air bag
44 expansion and contraction mechanism
50 power supply unit
51 battery
52 non-contact power reception unit
62 secondary side FPC substrate
100 sphygmomanometer
112 non-contact power transmission unit
121 shaft
152 memory
171 clip
200 charging device
300 charging unit for sphygmomanometer

The invention claimed is:

1. A charging unit comprising:
a sphygmomanometer comprising:
an expandable/contractable fluid bag supplied with fluid;
a bag-shaped cover body that accommodates the fluid bag, wherein the bag-shaped cover body is configured to attach the fluid bag to a site to be measured;
an expansion and contraction mechanism for expanding and contracting the fluid bag; and
a power supply unit comprising:
a secondary battery for supplying driving power to the expansion and contraction mechanism, and
a power reception unit for receiving power for charging the secondary battery,
wherein the power supply unit is arranged in the bag-shaped cover body,
wherein the power reception unit is supplied with power through an electromagnetic inductive action from a power transmission unit arranged in a non-contact state with the power reception unit, and wherein the power reception unit is arranged in a zone between one end of the fluid bag and an end of the bag-shaped cover body so that the power reception unit does not overlap with the fluid bag;
a charging device for charging the secondary battery, wherein the charging device comprises:
 a positioning unit positioned with respect to the bag-shaped cover body; and
 the power transmission unit arranged to face the power reception unit in a non-contact state when the positioning unit is positioned with respect to the bag-shaped cover body,
wherein the bag-shaped cover body has a hollow tubular shape with a display unit mounted on an outer surface of the bag-shaped cover body and the power reception unit located adjacent the display unit, and
wherein the positioning unit is a shaft member having a solid tubular shape with the power transmission unit arranged on an outer peripheral surface of the shaft member, so that when the shaft member is inserted into the hollow tubular bag-shaped cover body, the power transmission unit and the power reception unit are positioned to face each other.

2. The charging unit according to claim 1, wherein the expansion and contraction mechanism is arranged inside the bag-shaped cover body.

3. The charging unit according to claim 1,
wherein the power reception unit comprises a flexible substrate having flexibility, and
wherein the flexible substrate is formed with a coil on a surface of the flexible substrate.

4. The charging unit according to claim 1, wherein the power reception unit comprises a power transmission and reception function enabling transmission and reception of power when a plurality of power reception units are positioned proximate to each other between a plurality of sphygmomanometers.

5. A charging unit comprising:
a sphygmomanometer comprising:
 an expandable/contractable fluid bag supplied with fluid;
 a bag-shaped cover body that accommodates the fluid bag, wherein the bag-shaped cover body is configured to attach the fluid bag to a site to be measured;
 an expansion and contraction mechanism for expanding and contracting the fluid bag; and
 a power supply unit comprising:
  a secondary battery for supplying driving power to the expansion and contraction mechanism, and
  a power reception unit for receiving power for charging the secondary battery,
 wherein the power supply unit is arranged in the bag-shaped cover body,
 wherein the power reception unit is supplied with power through an electromagnetic inductive action from a power transmission unit arranged in a non-contact state with the power reception unit, and
 wherein the power reception unit is arranged in a zone between one end of the fluid bag and an end of the bag-shaped cover body so that the power reception unit does not overlap with the fluid bag;
a charging device for charging the secondary battery, wherein the charging device comprises:
 a positioning unit positioned with respect to the bag-shaped cover body; and
 the power transmission unit arranged to face the power reception unit in a non-contact state when the positioning unit is positioned with respect to the bag-shaped cover body,
wherein the positioning unit is a clip member having a U-shape with two arms that sandwich the bag-shaped cover body from one side edge thereof, and
wherein the power transmission unit is mounted in one of the two arms of the U-shaped clip member and the power reception unit is arranged in the bag-shaped cover body at a location where the two arms of the clip member sandwich.

6. The charging unit according to claim 1, wherein the power reception unit and the power transmission unit have a communication function for enabling wireless communication between the sphygmomanometer and the charging device.

7. The charging unit according to claim 6, wherein the charging device further comprises a memory for storing information communicated from the power reception unit toward the power transmission unit.

* * * * *